(12) United States Patent
Simmet (10) Patent No.: US 7,718,124 B2
(45) Date of Patent: May 18, 2010

(54) COUNTING, VIABILITY ASSESSMENT, ANALYSIS AND MANIPULATION CHAMBER

(75) Inventor: Ludwig O Simmet, Verona, WI (US)

(73) Assignee: Minitube of America, Inc., Verona, WI (US)

( * ) Notice: Subject to any disclaimer, the term of this patent is extended or adjusted under 35 U.S.C. 154(b) by 1342 days.

(21) Appl. No.: 11/142,929

(22) Filed: Jun. 2, 2005

(65) Prior Publication Data

US 2006/0275743 A1     Dec. 7, 2006

(51) Int. Cl.
    *G01N 31/22*     (2006.01)
    *G01N 21/03*     (2006.01)
    *G01N 21/01*     (2006.01)
    *G01N 1/00*     (2006.01)
    *G01N 33/48*     (2006.01)
    *C12M 3/00*     (2006.01)
    *B01L 11/00*     (2006.01)

(52) U.S. Cl. ............ 422/57; 422/58; 422/101; 436/165; 435/287.2; 356/36; 356/39; 356/246; 359/398

(58) Field of Classification Search ............ 422/57, 422/101, 58; 436/165; 359/398; 356/246, 356/39, 36; 435/287.2
See application file for complete search history.

(56) References Cited

U.S. PATENT DOCUMENTS

| 1,480,391 | A | * | 1/1924 | Hausser | 356/39 |
| 3,432,275 | A | | 3/1969 | Unger | 23/292 |
| 3,705,000 | A | | 12/1972 | Guerra | 356/246 |
| 3,829,216 | A | | 8/1974 | Persidsky | 356/36 |
| 3,961,346 | A | | 6/1976 | White | 356/244 |
| 4,441,793 | A | | 4/1984 | Elkins | 350/536 |
| 4,607,321 | A | * | 8/1986 | Obi | 363/41 |

(Continued)

FOREIGN PATENT DOCUMENTS

DE     4403308 A1     8/1995

(Continued)

OTHER PUBLICATIONS

Hamilton Thorne Biosciences, Inc., 2X-CEL Chamber, 2 pages at http://www.hamiltonthorne.com/cgi-bin/printview/printview.pl (Apr. 23, 2004).

(Continued)

*Primary Examiner*—Lore Jarrett
(74) *Attorney, Agent, or Firm*—Whyte Hirschboeck Dudek SC (57) ABSTRACT

A transparent plastic slide has a recessed chamber which receives a transparent plastic cover. The cover has a fluid inlet opening which overlies a recessed center well in the slide. The well has a sloping ramp which extends to a viewing platform which has a surface which is closely spaced from the underside of the cover to define a constant thickness viewing cavity surrounding the well. An overflow channel surrounds the viewing platform. A vent hole extends through the cover above the overflow channel. The sample is introduced into the center well through the fluid inlet opening. The fluid flows into the viewing cavities by capillary action, and is free to overflow the viewing cavities and be received within the overflow channel, thus reducing boundary effects. An inlet port may be provided above the viewing platform to permit substances to be added to a sample while it is under observation.

28 Claims, 5 Drawing Sheets

U.S. PATENT DOCUMENTS

| | | | | |
|---|---|---|---|---|
| 4,761,381 | A | * 8/1988 | Blatt et al. | 436/165 |
| 4,775,515 | A | * 10/1988 | Cottingham | 422/73 |
| 4,790,640 | A | * 12/1988 | Nason | 359/396 |
| 4,911,782 | A | 3/1990 | Brown | 156/633 |
| 5,200,152 | A | 4/1993 | Brown | 422/102 |
| 5,229,163 | A | * 7/1993 | Fox | 204/169 |
| 5,306,467 | A | 4/1994 | Douglas-Hamilton et al. | 422/99 |
| 5,349,436 | A | 9/1994 | Fisch | 356/246 |
| 5,503,803 | A | 4/1996 | Brown | 422/102 |
| 5,569,607 | A | 10/1996 | Simon et al. | |
| 5,948,673 | A | * 9/1999 | Cottingham | 435/287.2 |
| 6,052,224 | A | * 4/2000 | Richardson | 359/398 |
| 6,445,451 | B1 | 9/2002 | Douglas-Hamilton et al. | 356/425 |
| 6,551,554 | B1 | 4/2003 | Vermeiden et al. | 422/58 |

FOREIGN PATENT DOCUMENTS

| | | |
|---|---|---|
| JP | 063019532 | 1/1988 |
| JP | 9-236756 A | 9/1997 |
| JP | 09236756 | 9/1997 |

OTHER PUBLICATIONS

Conception Technologies, MicroCells, 2 pages (2001) at http://www.conceptiontechnologies.com/product_template.asp?id=47.

Conception Technologies, Frequently Asked Questions (Andrology . . . Microcell (at p. 3)), 7 pages (2001) at http://www.conceptiontechnologies.com/faqs.asp.

Sefi-Medical Instruments, Makler Counting Chamber, Instructions for Use.

* cited by examiner

COUNTING, VIABILITY ASSESSMENT, ANALYSIS AND MANIPULATION CHAMBER

CROSS REFERENCES TO RELATED APPLICATIONS

Not applicable.

STATEMENT AS TO RIGHTS TO INVENTIONS MADE UNDER FEDERALLY SPONSORED RESEARCH AND DEVELOPMENT

Not applicable.

BACKGROUND OF THE INVENTION

The present invention relates to devices for displaying specimens for examination under magnification in general, and more particularly to such devices for counting, manipulation, and making viability assessment of cells.

With an increasing demand for quality agricultural products in an increasingly competitive agricultural market, animal artificial insemination (AI) techniques are becoming widespread as an effective means to achieve improved quality of stock, while at the same time reducing the costs and labor involved in natural breeding techniques.

AI techniques require the collection of semen from a producing male animal, and insemination of the female animal at a later time, and usually at a location more or less remote from the collection site. A consequence is that the semen to be used may be subject to degradation or decay due to the effects of temperature, time, or stress of shipment and storage. It is therefore necessary to analyze the quantity and vigor of the sperm within a sample, in assessing the fertilizing qualities of a particular ejaculate at the producing end, as well as in some cases in the insemination end.

One test is to count the quantities of active or motile sperm within a given volume of semen. The counting is carried out under a microscope or through the use of a photometer or with a photometer, and only considers a very small subset of the entire sample. However, because the subject of the count is moving, the presence of boundaries on the counting area can disadvantageously complicate the counting procedure. If the counting area constrains the sample within boundaries, the presence of the boundaries can affect the accuracy of the counting procedure because of the effect the boundaries have on the distribution of the sperm within the sample area. Some sperm for example will concentrate adjacent to a boundary.

Certain cell counters, or haemocytometers, minimize boundaries by placing a single drop of liquid sample between two precision formed optical plates. These devices, however, are very costly, and hence must be sterilized and reused. Other, disposable devices employ a screen-printed layer to define channels between a slide and a cover. However, these devices usually rely exclusively on capillary action for loading, and must be handled carefully to avoid the introduction of air bubbles which would prevent the complete filling of the specimen chambers. Moreover, prior art devices often accommodate only a very small quantity of liquid, sometimes as little as 1.3 µl, which makes analyses which take more than a few minutes to conduct problematic, as the specimen can dry out. Especially, when in the case of sperm cells, the specimen is maintained above room temperature on a heated microscope stage.

In addition, conventional devices are not readily loaded while under observation, making comparative analyses of specimens before and after the addition of some substance difficult.

What is needed is a low-cost disposable device for presenting a thin layer of known thickness of a sample allowing repeatable and accurate visual measurements to be made on the sample.

SUMMARY OF THE INVENTION

The analysis device of this invention provides a cost-effective disposable analysis tool to facilitate counting or assessing cells within a defined volume of fluid sample, for example to assist in artificial insemination techniques in livestock. A transparent plastic slide has at least one recessed chamber, but conveniently may have three. Each recessed chamber has a mating optically clear transparent plastic cover permanently affixed by the manufacturer. The cover has a fluid inlet opening which overlies a recessed center well in the slide. The slide center well has a smoothly sloping ramp which extends to an annular viewing platform which has a surface which is closely spaced from the underside of the cover to define a constant thickness viewing cavity between the cover and the slide viewing platform. The viewing platform surrounds the center well, and an overflow channel surrounds the viewing platform. A vent hole extends through the cover above the overflow channel so that the capillary action produced by the viewing cavity can act unimpeded by air trapped in front of an advancing capillary flow. The sample containing the cells or other elements which it is desired to analyze is introduced into the center well through the fluid inlet opening. The fluid flows into the viewing cavity by capillary action, and is free to overflow the viewing cavities and be received within the overflow channel. Observations of the number or qualities of the cells within the viewing cavities may be taken without the complications of boundaries adjacent to the region being observed. An obscuring surface treatment may be applied to the cover to help to direct the observer to only those spots in which the constant depth viewing cavities are visible. The cover may be provided with a secondary inlet port in the vicinity of the viewing cavity, through which dyes, antibiotics, or other chemicals or additives may be added to the sample, even while the specimen cells within the sample remain under observation. For extended observations, additional culture medium may be added through the fluid inlet opening.

It is a feature of the present invention to provide a disposable laboratory tool which facilitates the accurate observation of cells contained within a fluid sample.

It is another feature of the present invention to provide an economical tool which presents a defined volume of fluid sample at constant thickness for observation while avoiding the effect which edges within a viewing area may have on a sample or its constituent parts.

It is a further feature of this invention to provide a device to facilitate cell counting which may be rapidly and consistently filled with the sample to be analyzed.

It is also a feature of this invention to provide a device which permits extended duration observations of samples and which permits the sample culture medium to be supplemented while the sample is undergoing observation.

It is an additional feature of the present invention to provide a method of analyzing specimens under magnification both before and after the addition of substances which act upon the specimen.

Further features and advantages of the invention will be apparent from the following detailed description when taken in conjunction with the accompanying drawings.

DESCRIPTION OF THE PREFERRED EMBODIMENTS

Referring more particularly to FIGS. 1-10, wherein like numbers refer to similar parts, a device 20 which facilitates the analysis of specimens under magnification is shown in FIGS. 1-4. The device 20 may serve as a cell counter or haemocytometer, or may be used for other analyses of cells or non-living elements, especially for extended duration or comparative analyses. The device 20 has three identical analysis units 22. It should be understood that a single device 20 may have only one analysis unit 22 or a greater number as required. The device 20 has a stiff transparent slide 24 which may be about one inch by three inches. The slide has recessed circular chambers 26 which each receive a generally circular transparent cover 28. The chambers may be about 18.7 mm in diameter, and spaced from one another on one-inch centers. The slide may be about 2.4 mm thick, while the cover may be about 0.6 mm thick.

Both the covers 28 and the slide 24 may be formed of any suitably rigid transparent non-toxic material, for example Cyclic Olefin Copolymers (COC), which can be fabricated with optical grade clarity. The plastic used may also be polycarbonate. Note that there is preferably a parallel relationship between the unobscured viewing region 78 surface, the lower surface 32 of the cover 28, and the viewing platform annular surface 48.

Figure 2:
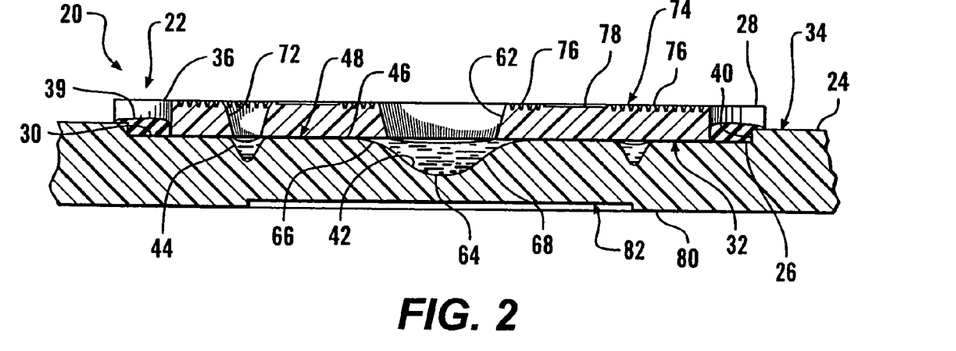
FIG. 2 is a cross-sectional view of the device of FIG. 1 with a liquid sample received therein, and taken along section line 2-2.
Figure 7:
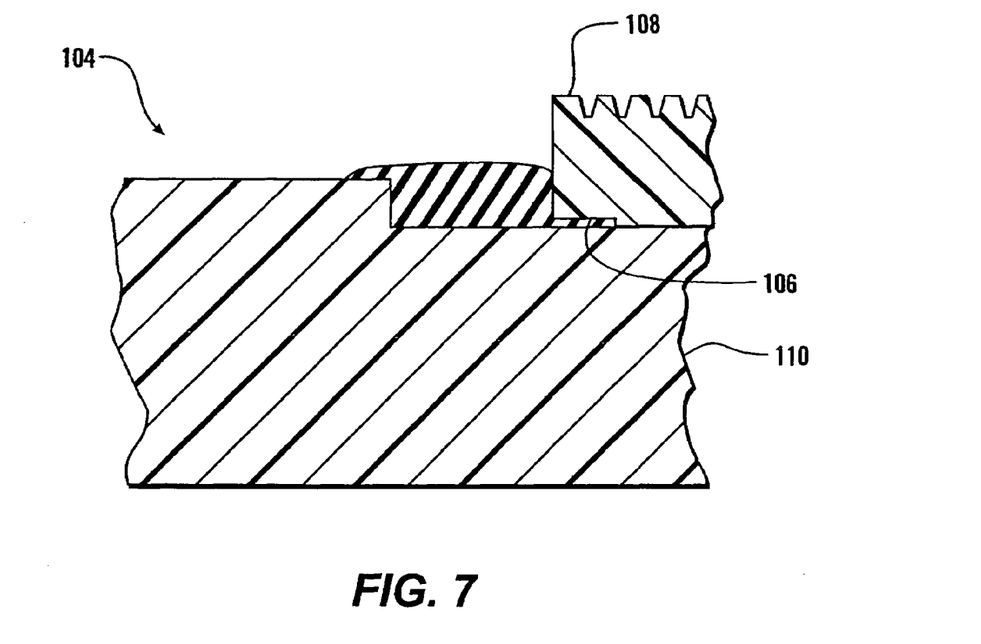
FIG. 7 is an enlarged fragmentary cross-sectional view of an alternative embodiment device of this invention, having a glue receiving recess on the underside of the cover perimeter.

The slide 24 has an upper surface 30 within each chamber 26 which engages a lower surface 32 of the cover 28. The upper surface 30 of the chamber 26 is preferably recessed below a slide top surface 34, as shown in FIG. 2. A side wall 38 extends between the upper surface 30 of the chamber 26 and the top surface 34 of the slide. Projections 40 extend radially inwardly from the side wall 38, and the projections are received within radially inwardly extending notches 36 formed in the covers 28. The cover 28 may be secured to the slide 24 by an adhesive resin 39 disposed in the notches 36, as the notches are larger than the projections 40 received therein. The cover is secured to the slide by the manufacturer, and thus the end user does not need to attach the cover, or handle adhesives. As shown FIG. 2, the adhesives do not come in contact with the sample. The adhesive resin 39 is preferably a solvent based adhesive, but UV curable adhesives, or laser welding may also be used to attach the cover to the slide. As shown in FIG. 7, a device 104 may be similar to the device 20, but may have a peripheral glue receiving recess 106 on the underside of the cover 108. The cover 108 is thus adhered directly to the slide 110.

Figure 4:
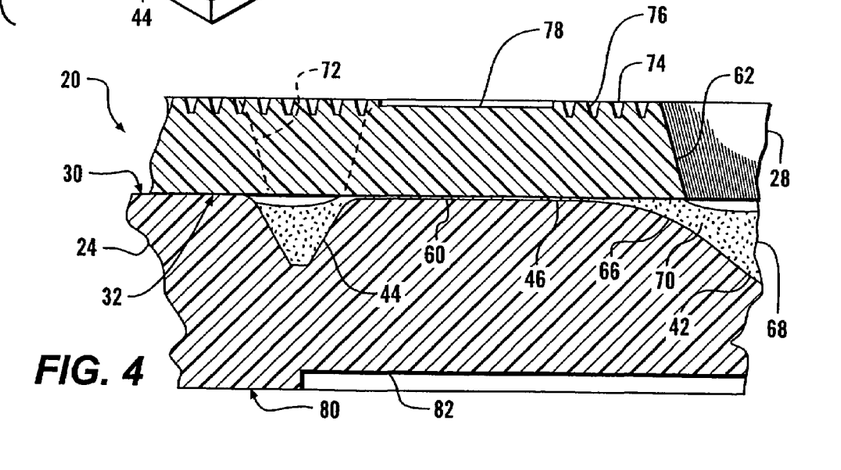
FIG. 4 is an enlarged cross-sectional view of the device of FIG. 1, taken along section line 4-4.

Each chamber 26 has a center well 42 which is recessed below the chamber upper surface 30. The chamber upper surface 30 is that portion of the slide which engages the lower surface 32 of the cover 28 and which is at a level higher than the level of a viewing platform 46. A ringlike overflow channel 44 encircles the center well 42, and is separated from the center well by the annular viewing platform 46 which encircles the center well. The overflow channel 44 is recessed, as best shown in FIG. 4, below the viewing platform 46. The viewing platform 46 has an annular planar surface 48 which is spaced a constant distance below the chamber upper surface 30, and hence below the overlying cover 28 lower surface 32. The center well 42 is depressed below the level of the viewing platform surface 48. A viewing cavity 60 is thus defined between the viewing platform upper surface 48 and the lower surface 32 of the transparent cover 28. This cavity also serves as a capillary flow channel in fluid communication with the well 42 and the overflow channel 44.

The distance between the viewing platform surface 48 and the chamber upper surface 30 is very small, generally about 5 to 50 microns, preferably about 12 microns or 20 microns, although devices with different spacing may be constructed to best accommodate a particular cell to be observed, 12 microns being adapted for boar semen, while 20 microns would be appropriate for rat semen. The thickness of the viewing cavity is thus defined between the underside of the cover and the planar surface 48 of the viewing platform 46.

Figure 6:
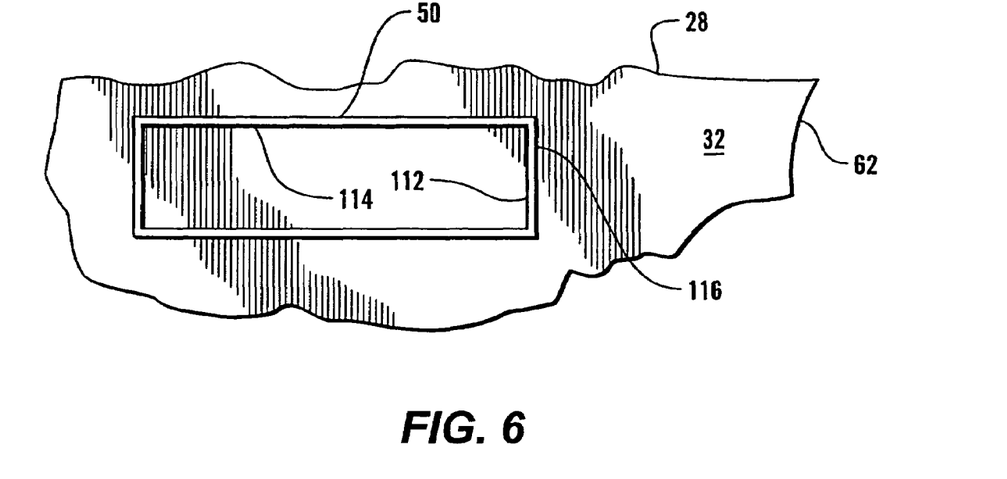
FIG. 6 is an enlarged fragmentary plan view of the underside of the cover of FIG. 1, showing a single rib.

To contribute to the maintenance of this uniform spacing, radially extending ribs 50 may be provided projecting downwardly from the lower surface 32 of the cover 28. The ribs 50 have the same thickness as the spacing of the viewing platform below the chamber upper surface 30. The ribs 50 abut against the viewing platform and maintain the desired spacing in viewing cavities 60 defined between the viewing platform surfaces 48 and the lower surface 32 of the cover and between the ribs 50. The viewing cavities are in fluid communication with both the center well 42 and the overflow channel 44. As shown in FIG. 6, the ribs 50 may be formed as narrow closed rings of rib side wall 112. The rib side wall 112 thus defines a rib interior volume 114 beneath the cover lower surface 32, and a rib exterior volume 116 exterior to the rib.

Figure 3:
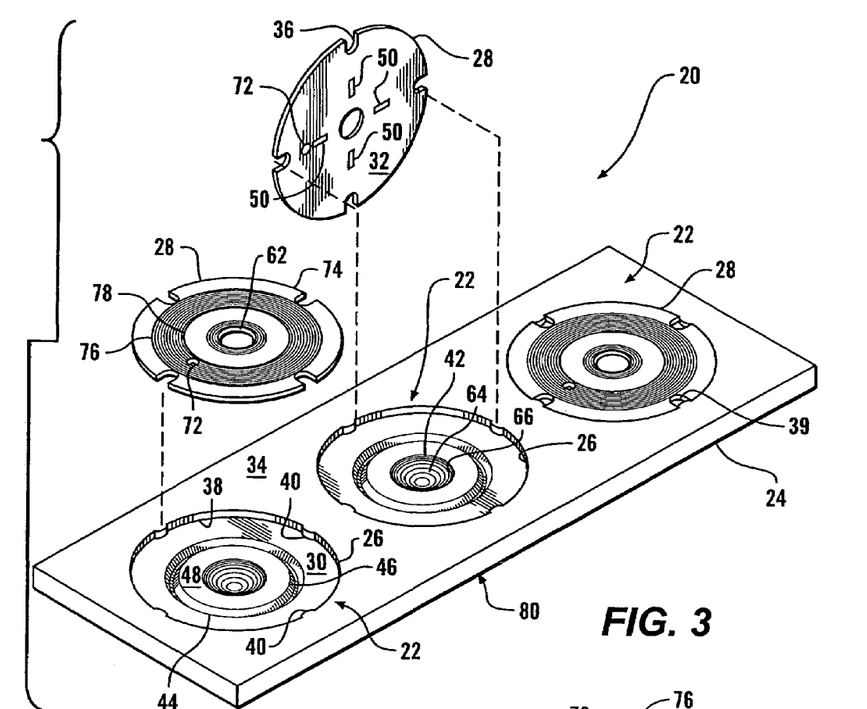
FIG. 3 is an exploded isometric view of the device of FIG. 1, with two of the covers exploded from the slide, and one cover shown in an assembled position.

As shown in FIG. 3, the cover 28 has a fluid sample inlet opening 62 which is a tapered opening, about ⅛th inch in diameter. The inlet opening 62 serves as a loading orifice for the device's analysis unit 22, and is centered over the-center well 42. The center well 42 is a smooth concave dish, as best shown in FIG. 2. The center well may be about 6 mm in diameter. The fluid inlet opening 62 is centered over the central region 64 of the center well 42, which is the deepest portion of the center well. A continuous sloped lead-in ramp 66 extends between the central region 64 and the viewing platform surface 48. There are no ridges or discontinuities on the center well 42, and hence the free flow of fluid is not impeded.

A fluid sample 68 containing cells 70, such as sperm, is introduced into the well through the inlet opening 62. A conventional pipette may be used to dispense the sample into the inlet opening. The sample which may be as large as about 20 μl is introduced slowly into the device 20. The center well 42 may have a volume of approximately 7 μl. The sample is dispensed into the center well from the pipette generally such that the fluid level extends above the level of the chamber upper surface 30. The fluid is drawn by capillary action between the cover and the viewing platform up the sloped lead-in ramp and into the viewing cavities 60. However, in addition to the capillary action, the depth of the center well 42 also provides a hydraulic force which drives the sample into the viewing cavities 60. Because there are no walls to obstruct the liquid flow, the system equilibrates very quickly. The fluid passes through the viewing cavities and overflows into the surrounding overflow channel 44. To avoid resistance to fluid flow by air trapped within the overflow channel 44, a vent hole 72 extends through the cover 28 in a position directly over the overflow channel. As shown in FIG. 2, the vent hole communicates with the overflow channel permitting the escape of air as fluid passes into the overflow channel from the viewing cavities 60. The vent hole 72 may be about 1 mm in diameter.

It will be noted that the fluid in the viewing cavities 60 is not restrained either on the side of the center well or on the side of the overflow channel. It is therefore possible to obtain an accurate count of cells in motion without having to take into consideration cells rebounding from a fixed boundary. The boundaries to the viewing cavities 60 presented by the ribs 50 are comparatively small, and care may be taken in the course of the observations to make a count in a region sufficiently spaced from a rib to minimize any impact on such a boundary. In addition, the device may be fabricated without ribs if desired. It should be noted that when used in analysis of sperm cells, the sperm cells will generally be in motion while under observation, and sperm cells can pass into the overflow channel from the viewing platform, and can pass from the overflow channel back on to the viewing platform.

Figure 1:
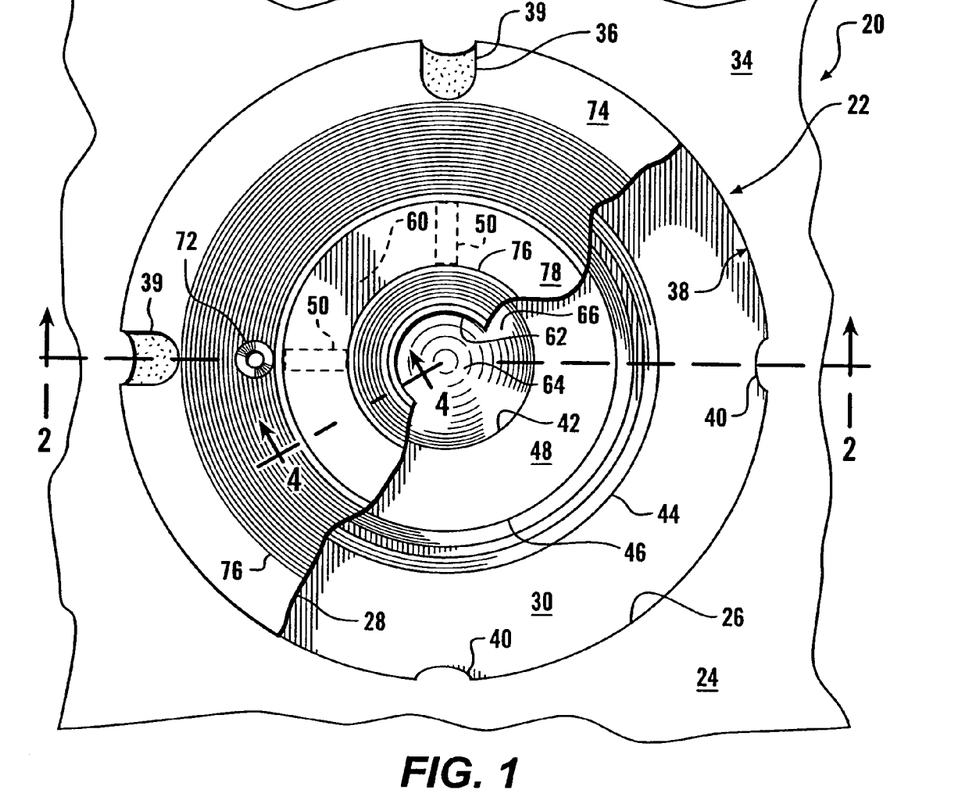
FIG. 1 is a fragmentary top plan view of the analysis device of this invention, partially broken away in section.

To assist the observer in making observations only in the shallow region of the viewing cavities 60, the upper surface 74 of the cover 28 is preferably provided with an obscuring surface treatment 76 on portions of the cover which surround a ring-like unobscured viewing region 78. The obscuring surface treatment 76 may be a series of concentric shallow ring-like depressions, as shown in FIG. 1. An etched or frosted effect may also be employed for the obscuring surface treatment 76.

Because of the very careful observations which must be taken under magnification, it is desirable that the viewing platform surface 48, the surfaces of the cover, and the underside 80 of the slide be as clear and unobstructed as possible. These surfaces should be optical grade quality. Surfaces required to be optically clear may be fabricated by polishing the forming mold to the required degree. Typically, the covers and the slide will be formed in an injection molding process. Those parts of the device through which observations are taken should be formed in molds which have been accurately polished to avoid blemishes that would excessively detract from the optical properties of the device. The mold surfaces may be formed with diamond fly cutting and turning machines, such as is performed by the NetOptix division of Corning Incorporated, www.corningnetoptix.com. Although not necessary when used with automated counting systems, a grid may be formed in the cover or slide to facilitate counting cells within a defined region of a viewing cavity 60.

To protect against scratches to the underside 80 of the slide, a relieved region 82, as shown in FIG. 2, may be formed beneath the viewing cavities 60. The relieved region keeps the underside 80 spaced from immediate contact with a tabletop, the microscope stage, etc., and helps to avoid scratching. The depth of the relief is sufficiently small that the heat from a heated microscope stage is not appreciably impeded in reaching the sample. To make the observations, the device 20 will be placed on an illuminated platform below a microscope objective. Alternatively, the device may be used with video based systems for sperm counting.

Because of the low cost of a device which is made from molded plastic parts, the device 20 may be readily disposed of after use. By being disposable, not only is the expense of cleaning the device eliminated, but also the possibility of contaminating samples with material from previous uses.

Although the ribs 50 may be solid downward protrusions, the construction of each rib as a closed ring of narrow rib side wall 112 permits the ribs to serve as a quality control measure in assembling the device 20. It will be observed that if the cover is properly attached by adhesive to the slide, the rib side walls 112 will engage against the slide so as to form a liquid tight seal. If due to some manufacturing error a liquid tight seal is not obtained, then, once liquid is introduced into the device, liquid may enter the rib interior volume 114 of a rib. This entrance of liquid into the rib interior volume will be detectable under magnification, and will signal to the user of the device that it is defective, allowing the user to discard the defective unit and continue observations with a new one.

As shown in FIG. 6, the ribs 50 may be formed as narrow closed rings of rib side wall 112. The rib side wall 112 thus defines a rib interior volume 114 beneath the cover lower surface 32, and a rib exterior volume 116 exterior to the rib.

It should be noted that, although the device of this invention has been shown as generally circular, linear or other patterns are also possible.

Figure 5:
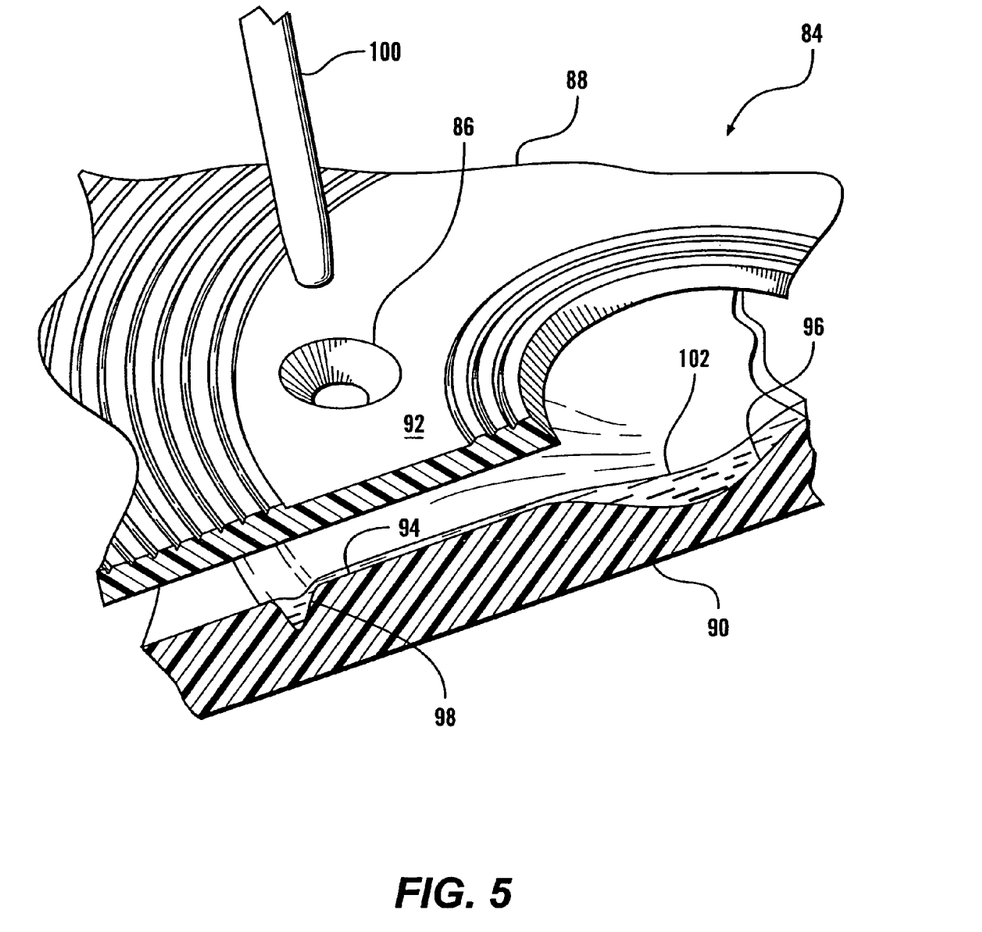
FIG. 5 is a fragmentary perspective view, partially broken away in section, of an alternative embodiment specimen chamber of this invention, shown with a pipette in exploded view.

An alternative embodiment device 84 which permits the ready addition of substances such as chemicals, active components, dyes, antibiotics or other additives, to a sample under observation is shown in FIG. 5. The device 84 may be identical to the device 20, except that a secondary inlet port 86 is provided in the transparent cover 88 which overlies the slide 90. The inlet port 86 is a small diameter opening positioned in the unobscured viewing region 92 of the cover 88 to directly overlie the viewing platform 94 which is positioned between the central well 96 and the overflow channel 98. The inlet port 86 receives the tip of a pipette 100 to permit the introduction of substances to the sample 102 under observation. The device 84 thus allows a portion of the sample 102 to be observed prior to, during, and after the introduction of some substance which may alter the appearance of the sample.

The device 84 is particularly helpful for determining the effect of particular additives on living specimens by observation while an additive infuses the culture medium. For example in pharmacological stress testing, a medication or pharmaceutical product is tested for its effects on sperm motility. For example, a boar semen specimen may be observed on the viewing platform 94 and the motility of the sperm cells assessed and recorded. Some additive substance may then be introduced into the sample on the viewing platform by injecting an additive through the inlet port. Then substantially the same sperm cells which had been previously observed can be analyzed immediately after their contact with the additive. Such a technique may also be particularly useful in analysis procedures which require dying or staining the sample in order to observe particular features of the sample. For example, in multi-photon excitation microscopy or confocal (single photon excitation) microscopy low levels of light are used to excite a fluorescent dye added to the sample. The dye, although making certain features of the sample more apparent, can have detrimental effects on living samples. The device 84 permits the vigor and biological features of the sample to be carefully observed first, and then the special features only visible with the dye treatment to be observed. Any deleterious impact of the dye can thus be assessed and corrected for. The device can also be used for efficacy testing of antibiotics and other substances, where the reactions of the cells under observation can be viewed over time. For example, undesirable bacteria could be viewed in the viewing cavities, while a particular antibiotic or concentration of antibiotic is added through the secondary inlet port. The effect of the antibiotic on the growth of the bacteria could then be determined, without the need to remove the device from the microscope stage.

It should be noted that many types of plastic are naturally somewhat hydrophobic, with the result that capillary action of liquid is restrained between two sheets of these types of plastic. To overcome this property of some plastic, the material may need to be treated in a conventional fashion to be made more hydrophillic. This treatment may include applying a oxygen plasma to the surface, or some type of corona treatment, or a gas plasma deposition of inert layers of metal, such as gold.

Figure 8:
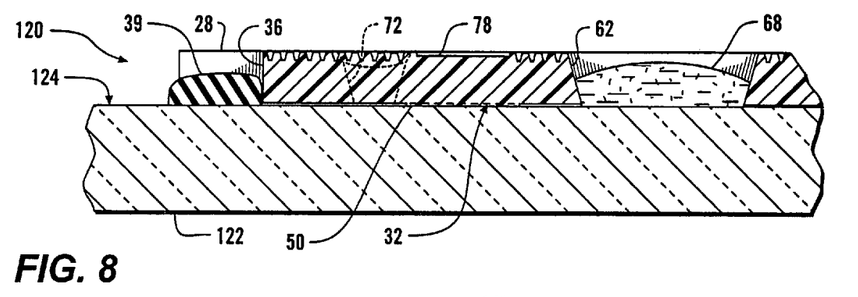
FIG. 8 is a cross-sectional view of an alternative embodiment device of this invention, in which the cover of FIG. 1 is adhered to a conventional glass slide.
Figures 9, 10:
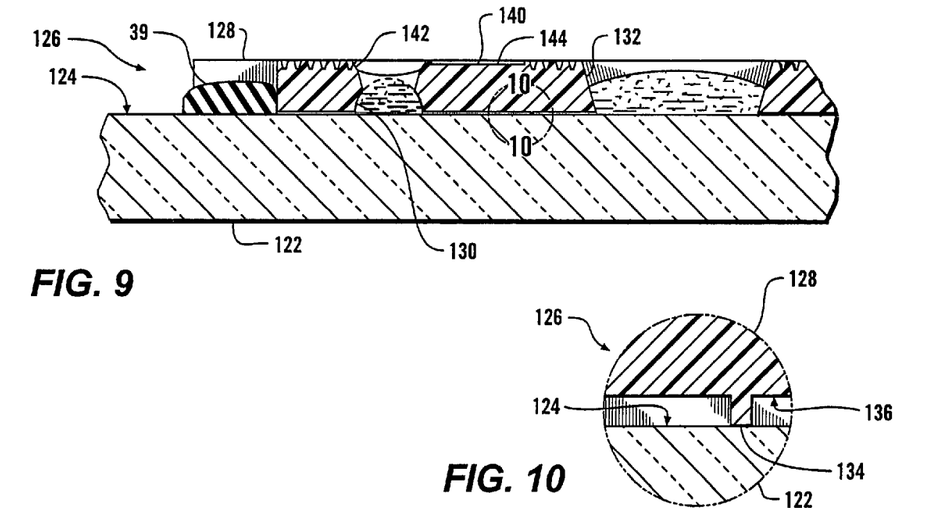
FIG. 9 is a cross-sectional view of an alternative embodiment device of this invention having a cover with an inverted channel positioned radially outwardly of the observation region.
FIG. 10 is an enlarged view of the device of FIG. 9, taken at section 10-10, to show the structure of a portion of a spacing rib.

To obtain the desirable hydrophilic properties of glass, a plastic cover of this invention may be used in connection with a glass slide, as in the devices 120, 126, shown in FIGS. 8 and 9. The device 120, shown in FIG. 8, affixes the cover 28 of the device 20 directly to a conventional glass slide 122. The ribs 50 serve to space the lower surface 32 of the cover 28 the desired uniform distance above the upper surface 124 of the glass slide 122. Adhesive resin 39 fixes the cover to the slide 122. However, the adhesive is positioned only within the notches 36, leaving the remainder of the perimeter of the cover open to the exterior. When the fluid sample 68 is introduced into the sample inlet opening 62, the sample inlet opening serves as a center well. The sample 68 is then urged to flow beneath the viewing region 78, both by capillary action and by the hydraulic force of the sample within the inlet opening. The vent hole 72 which is in communication with the lower surface of the cover 28, permits excess quantities of sample to flow upwardly therein, and also prevents air captured beneath the cover from forming a bubble that would block the flow of sample. It is acceptable for a small portion of the sample to pass outwardly from under the cover around the periphery.

The alternative embodiment device 126, shown in FIGS. 9 and 10, also employs a conventional glass slide 122, but differs from the device 120 in having a plastic cover 128 with an upwardly extending overflow channel 130. The overflow channel 130 is a semi-annular relieved region which is positioned to encircle the sample inlet opening 132. The overflow channel 130 provides a volume which receives sample which is introduced through the inlet opening 132. The downwardly protruding ribs 134, shown in FIG. 10, space the lower surface 136 of the cover 128 from the upper surface 124 of the glass slide 122. The cover 128 is affixed to the slide 122 by the adhesive resin 39 positioned within notches 138 at the periphery of the cover. The overflow channel 130 communicates with the upper surface 140 of the cover through a vent hole 142 which permits the escape of air bubbles. An unobscured viewing region 144 of the cover 128 is defined between the sample inlet opening 132 and the overflow channel 130. The spacing of the lower surface of the cover from the upper surface of the slide is maintained by the ribs 134 beneath the unobscured viewing region 144, and observations of the sample are taken in that region.

It should be noted that the cover 128 may be used in combination with the plastic slide 24 described above, such that the overflow channel 130 overlies the overflow channel 44, forming a combined channel above and below the upper level of the slide.

In any observation regimen which requires an extended period of time to conduct, in the range of thirty minutes or more, the effects of the heated microscope stage can cause the sample to begin to dry out, with an undesirable impact on living organisms. The devices of this invention are particularly suited to extended observations, because, although the region being observed within the viewing cavities is very shallow, the center well 42, 96 and the overflow channel 44 are significantly deeper, and provide for a greater capacity of sample. Moreover, additional fluid in the form of more culture medium can be added to the sample through the sample inlet opening 62 during the course of observation to make up for any evaporation of liquid.

In addition to being used for the analysis under magnification of elements within a fluid such as living organisms or cells in a culture medium, the device of this invention may be used in genomics and proteomics for the observation of other elements such as DNA fragments, proteins, etc. By offering the capability to observe the specimen while it is interacting with additives, the devices make cause and effect observations possible.

The present invention provides an advantageously larger sample volume than in many prior art devices. The larger volume sample will tend to compensate for the dilution error which is produced when the original specimen is diluted to make a sample suitable for examination under a microscope. In producing a diluted sample, there exists the possibility that the diluted sample will not be entirely homogenous, and may thus exhibit variations in cell concentration throughout the specimen. To the extent that it is possible to take a larger portion of the sample, these variations of concentration may be overcome. The devices of this invention effectively provide a vessel without walls, and an accurately spaced thickness of fluid which permits a dynamic flow of the sperm from reservoirs on multiple sides of the viewing platform. Such an arrangement is conducive to sperm movement and longer survival.

It is understood that the invention is not limited to the particular construction and arrangement of parts herein illustrated and described, but embraces all such modified forms thereof as come within the scope of the following claims.

I claim:

1. An apparatus structured for observation under magnification of elements present in a fluid, the apparatus comprising:

a transparent slide consisting of a single substrate and having an upper surface;

a transparent cover having a lower surface which overlies the upper surface of the slide;

a region in the slide defining a recessed center well which is recessed below the upper surface of the slide;

a region in the slide defining an overflow channel which is recessed below the upper surface of the slide and spaced from the recessed center well;

a viewing platform in a region of the upper surface of the slide extending between the recessed center well and the overflow channel, wherein the cover further comprises an unobscured viewing region situated over the viewing platform, a viewing cavity region between the viewing platform and the lower surface of the cover, said viewing cavity region in fluid communication with the recessed center well and the overflow channel, wherein said viewing cavity region serves as a capillary flow channel;

a fluid inlet opening extending through the cover for passage of fluid therethrough into the recessed center well;

wherein fluid within the well can be drawn through the viewing cavity region and into the overflow channel, and elements present in the fluid within the viewing cavity region can be observed.

2. The apparatus of claim 1, further comprising at least one vent hole extending through the cover in communication with the overflow channel.

3. The apparatus of claim 1, wherein the viewing platform encircles the recessed center well and the overflow channel encircles the viewing platform.

4. The apparatus of claim 1, further comprising a plurality of ribs which extend from the lower surface of the cover and engage the viewing platform of the slide, the ribs being of about constant thickness.

5. The apparatus of claim 1, wherein the slide comprises at least one projection which engages with a positioning notch on the cover to position the cover over the slide.

6. The apparatus of claim 5 further comprising adhesive disposed between the at least one projection and the positioning notch to secure the cover to the slide.

7. The apparatus of claim 1, wherein the cover further comprises an obscuring surface treatment surrounding the unobscured viewing region.

8. The apparatus of claim 1, wherein the lower surface of the cover is spaced from the viewing platform by a distance of approximately 12 microns.

9. The apparatus of claim 1, wherein the lower surface of the cover is spaced from the viewing platform by a distance of approximately 20 microns.

10. The apparatus of claim 1, wherein the recessed center well comprises a central region depressed below the viewing platform, and a continuous sloped lead-in ramp extending between the central region of the well and the viewing platform.

11. The apparatus of claim 1, wherein the slide and the cover comprise a plastic material.

12. The apparatus of claim 11, wherein the plastic material comprises a Cyclic Olefin Copolymer.

13. The apparatus of claim 11, wherein the plastic comprises a polycarbonate.

14. The apparatus of claim 1, further comprising a secondary inlet port extending through the cover for introduction of a substance into the viewing channel.

15. The apparatus of claim 1, wherein the viewing platform is recessed below the upper surface of the slide.

16. The apparatus of claim 1, further comprising a relieved region in the underside of the slide situated beneath the viewing cavity region.

17. An apparatus structured for observation under magnification of elements present in a fluid, the apparatus comprising:

a transparent slide consisting of a single substrate and having an upper surface, a region in the slide defining a recessed center well which is recessed below the upper surface of the slide, a region of the upper surface of the slide defining a viewing platform surrounding the recessed center well, the cover further comprising an unobscured viewing region situated over the viewing platform, a region in the slide defining an overflow channel which is recessed below the viewing platform and surround the viewing platform; and a transparent cover fixed to the slide and spaced above the viewing platform of the slide;

a viewing cavity region between the viewing platform of the slide and the cover, the viewing cavity region in fluid communication with the recessed center well and the overflow channel; and a fluid inlet opening extending through the cover to above the recessed center well for passage of fluid therethrough into the recessed center well;

wherein fluid within the recessed center well can be drawn through the viewing cavity region and into the overflow channel, and elements present in the fluid within the viewing cavity region can be observed.

18. The apparatus of claim 17, further comprising a vent hole extending through the cover in communication with the overflow channel.

19. The apparatus of claim 17, further comprising a plurality of ribs which extend from a surface of the cover and engage the viewing platform of the slide, the ribs extending downwardly to an about constant thickness.

20. The apparatus of claim 17, further comprising at least one projection on the upper surface of the slide which engages with a positioning notch on the cover to position the cover over the slide.

21. The apparatus of claim 17, wherein the cover further comprises an obscuring surface treatment surrounding the unobscured viewing region.

22. The apparatus of claim 17, wherein the recessed center well of the slide comprises a central region depressed below the viewing platform, and a continuous sloped lead-in ramp extending between the central region of the recessed center well and the viewing platform.

23. The apparatus of claim 17, wherein the slide and the cover comprise a plastic material.

24. The apparatus of claim 17, further comprising a secondary inlet port extending through the cover for introduction of a substance into the viewing cavity region.

25. An apparatus structured for observation under magnification of elements present in a fluid, the apparatus comprising:

a transparent slide consisting of a single substrate and having an upper surface, a transparent cover comprising a lower surface which overlies the upper surface of the slide, a sample inlet opening extending through the cover to the upper surface of the slide, an overflow channel defining a relieved region positioned in the lower surface of the cover, wherein said overflow channel is spaced from the sample inlet opening, at least one vent hole extending through the cover in communication with the overflow channel, and an unobscured viewing region in the upper surface of the cover and positioned between the sample inlet opening and the overflow channel; and a viewing cavity region between the upper surface of the slide and the lower surface of the cover beneath the unobscured viewing region, the viewing cavity region in fluid communication with the sample inlet opening and the overflow channel such that fluid introduced into the sample inlet opening can be drawn through the viewing cavity region and into the overflow channel and elements present in the fluid within the unobscured viewing region of the cover can be observed.

26. The apparatus of claim 25, wherein the slide and the cover comprise a plastic material.

27. The apparatus of claim 25, wherein the slide comprises glass, and the cover comprises a plastic material.

28. The apparatus of claim 25, further comprising a secondary inlet port extending through the cover within the viewing region for introduction of a substance into a fluid situated within the capillary flow channel.

* * * * *